US005906599A

United States Patent [19]

Kaldany

[11] Patent Number: 5,906,599

[45] Date of Patent: May 25, 1999

[54] DEVICE FOR DELIVERING BIOLOGICAL AGENTS

[75] Inventor: Antoine Kaldany, Chestnut Hill, Mass.

[73] Assignee: InterMED, Inc., Chestnut Hill, Mass.

[21] Appl. No.: 08/552,467

[22] Filed: Nov. 9, 1995

[51] Int. Cl.[6] .......... A61M 5/00; A61M 25/00; A61M 31/00

[52] U.S. Cl. .......... 604/264; 604/49; 604/57; 604/60; 604/58

[58] Field of Search .......... 604/48, 49, 51, 604/52, 57–60, 68, 70, 72, 93, 95, 158–160, 164–166, 170, 264; 606/13–15

[56] References Cited

U.S. PATENT DOCUMENTS

| | | | |
|---|---|---|---|
| 387,480 | 8/1888 | Alleman . | |
| 737,293 | 8/1903 | Summerfeldt . | |
| 806,746 | 12/1905 | Miller . | |
| 2,634,726 | 4/1953 | Hanson . | |
| 2,705,949 | 4/1955 | Silverman . | |
| 3,477,423 | 11/1969 | Griffith . | |
| 3,606,878 | 9/1971 | Kellogg, Jr. . | |
| 3,662,754 | 5/1972 | Halloran . | |
| 3,995,619 | 12/1976 | Glatzer . | |
| 4,178,810 | 12/1979 | Takahashi . | |
| 4,402,308 | 9/1983 | Scott . | |
| 4,411,657 | 10/1983 | Galindo | 604/274 |
| 4,461,280 | 7/1984 | Baumgartner . | |
| 4,537,593 | 8/1985 | Alchas | 604/411 |
| 4,578,059 | 3/1986 | Fabricant et al. | 604/43 |
| 4,600,014 | 7/1986 | Beraha . | |
| 4,609,370 | 9/1986 | Morrison | 604/165 |
| 4,699,154 | 10/1987 | Lindgren . | |
| 4,700,692 | 10/1987 | Baumgartner . | |
| 4,701,164 | 10/1987 | Cassou et al. | 604/218 |
| 4,702,261 | 10/1987 | Cornell et al. . | |
| 4,735,611 | 4/1988 | Anderson et al. | 604/130 |
| 4,776,346 | 10/1988 | Beraha et al. . | |
| 4,820,267 | 4/1989 | Harman | 604/60 |
| 4,842,585 | 6/1989 | Witt | 604/158 |
| 4,871,094 | 10/1989 | Gall et al. . | |
| 4,881,551 | 11/1989 | Taylor . | |
| 4,900,303 | 2/1990 | Lemelson | 604/57 |
| 4,900,304 | 2/1990 | Fujioka et al. | 604/60 |
| 4,907,598 | 3/1990 | Bauer . | |
| 4,913,142 | 4/1990 | Kittrell et al. | 606/7 |
| 4,917,100 | 4/1990 | Nottke . | |
| 4,940,061 | 7/1990 | Terwilliger et al. . | |
| 4,958,625 | 9/1990 | Bates et al. . | |
| 4,986,814 | 1/1991 | Burney et al. | 604/164 |
| 5,127,419 | 7/1992 | Kaldany . | |
| 5,226,426 | 7/1993 | Yoon . | |
| 5,271,744 | 12/1993 | Kramer et al. | 604/51 |
| 5,304,119 | 4/1994 | Balaban et al. | 604/51 |
| 5,358,474 | 10/1994 | Kaldany | 604/57 |
| 5,364,365 | 11/1994 | Wortrich | 604/158 |
| 5,372,585 | 12/1994 | Tiefenbrun et al. | 604/57 |
| 5,405,324 | 4/1995 | Wiegerinck | 604/60 |
| 5,419,765 | 5/1995 | Weldon et al. | 604/57 |
| 5,562,613 | 10/1996 | Kaldany | 604/57 |

FOREIGN PATENT DOCUMENTS

| | | |
|---|---|---|
| 0207726 | 7/1987 | European Pat. Off. . |
| 91/10399 | 7/1991 | WIPO . |

*Primary Examiner*—Wynn Wood Coggins
*Assistant Examiner*—Jennifer R. Sadula
*Attorney, Agent, or Firm*—Hamilton, Brook, Smith & Reynolds, P.C.

[57] ABSTRACT

A device for delivering biological agents includes a cannula for insertion into tissue having a distal end with a notch formed therein. A flexible membrane extending across the cannula notch has a surface for supporting a quantity of a biological agent. A displacement member is disposed within the cannula for displacing the support surface of the membrane laterally with respect to the cannula to deliver the biological agent with precision to a tissue site or body cavity.

29 Claims, 5 Drawing Sheets

DEVICE FOR DELIVERING BIOLOGICAL AGENTS

BACKGROUND

Much effort has been expended in recent years to find an effective and superior way of administering drugs to patients' bodies. Products such as the transdermal patch and once-a-day orally administered pills that more precisely deliver drugs have been developed. Such products are a boon to patients for they boost the effectiveness of the drugs and limit side effects by precisely controlling how quickly drugs are released in the body; by keeping drugs at a constant level and by delivering them exactly where needed.

One such development is the injection or implantation of drugs in the form of in microscopic particles or pellets at a disease site. The drugs are encapsulated in polymers or fatty compounds, such as liposomes which permit slow release of the encapsulated drug over time thereby potentially lowering the drugs toxicity.

In addition, there are times when it is desirable to deliver a biological agent that is in a non-conventional form to a disease site such as a drug in a loose particulate form, or a quantity of cells, cell clusters or cellular extracts in a biocompatible solution. A particulate biological agent can be in a granular, powdered, or microsphere form. The problem with biological agents in these forms is that they are difficult to properly deliver to a diseased tissue site.

SUMMARY OF THE INVENTION

The present invention provides a novel device with a distal end insertable into the tissue or a body cavity of a patient for delivering both particulate and liquid biological agents in a quick, predictable, safe and easy manner without damaging the biological agent. This is important in the delivery of cells or microspheres. The biological agent delivery device includes a cannula having a longitudinally extending wall and a distal end with a notch opening formed in the wall near the distal end. A flexible membrane disposed within the cannula notch opening has a support/delivery surface for supporting a quantity of a biological agent. A displacement member is disposed within the wall of the cannula for axial movement therein to laterally displace the support surface of the flexible membrane to deliver the biological agent to the desired tissue site.

In preferred embodiments, the present invention biological agent delivery device further includes an outer tube mounted concentric with the cannula. The cannula is capable of sliding within the outer tube to retract or extend the cannula relative to the outer tube for enclosing the cannula notch within the outer tube for insertion into tissue or exposing the cannula notch beyond the outer tube to allow delivery of the biological agent after insertion into tissue. The flexible membrane is preferably a tubular member having a closed terminal end which extends within the cannula, with the support surface of the flexible membrane being located near the closed terminal end and positioned within the cannula notch. When the flexible membrane is in a non-displaced state, the support surface is indented into the flexible membrane to form a pouch. This pouch can optionally be preformed. The displacement member in one preferred embodiment is a piston which moves axially within the cannula for displacing the support surface. In another preferred embodiment, the displacement member is a fluid such as a liquid or a gas.

In still another preferred embodiment, the present invention biological agent delivery device is a flexible catheter with fiber optics being optionally provided within the cannula for delivering radiation to a desired tissue or body cavity site. A lens associated with the fiber optics enables viewing of regions external to the cannula.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

Figure 1:
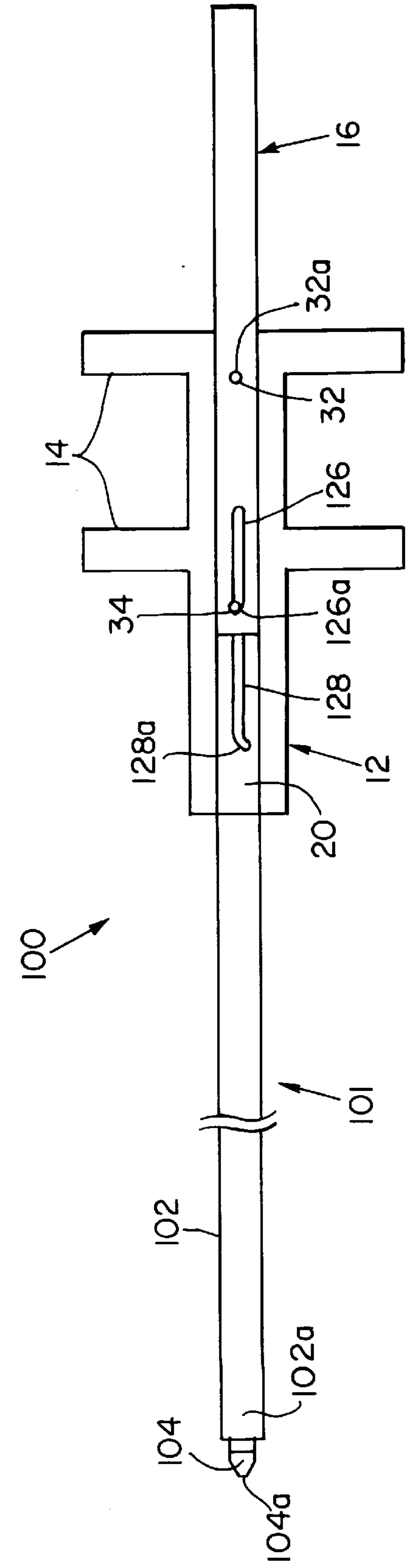
FIG. 1 is a plan view of the present invention biological agent delivery device.
Figure 2:
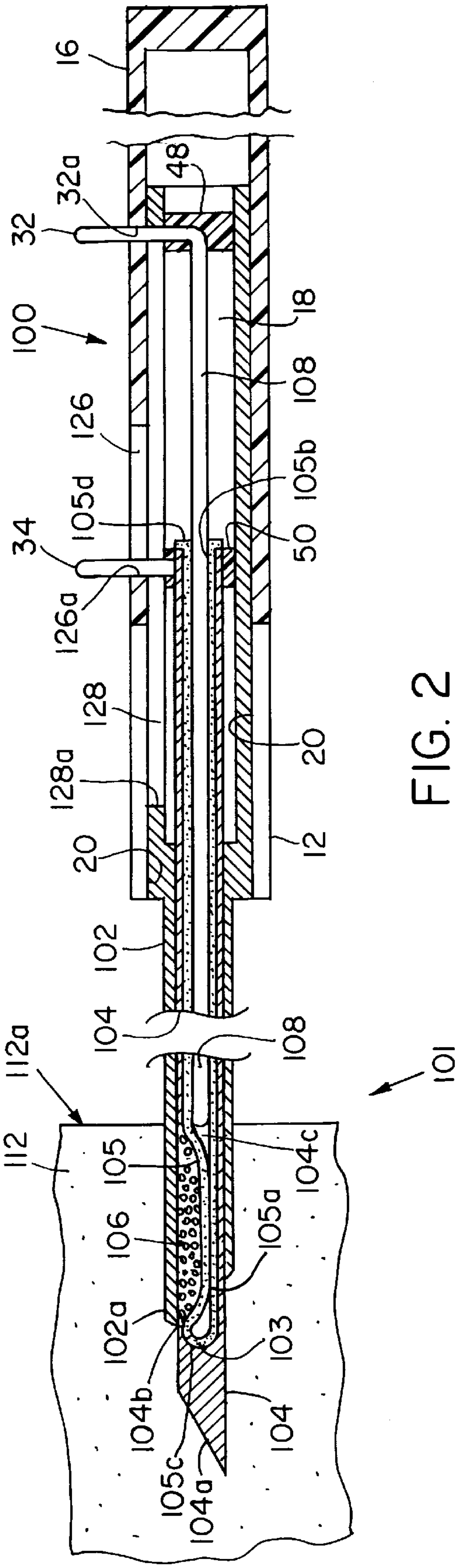
FIG. 2 is a side sectional view of the present invention biological agent delivery device with the distal end of the device inserted into tissue.

Referring to FIGS. 1 and 2, biological agent delivery device 100 is an apparatus suitable for single-handed subcutaneous delivery of a biological agent 106 such as a quantity of a loose particulate drug, or a quantity of cells, cell clusters or cellular extracts in solution with a biological compatible carrier. For purposes of illustrating the invention, we have selected a delivery device similar to the device disclosed in U.S. patent application Ser. No. 08/271,148 filed Jul. 6, 1994 which is incorporated herein by reference in its entirety. However, other mechanisms for inserting and retracting the various members may substitute therefore. Additionally, for illustration purposes, the biological agent 106 depicted in the drawings is a particulate drug.

Figure 3:
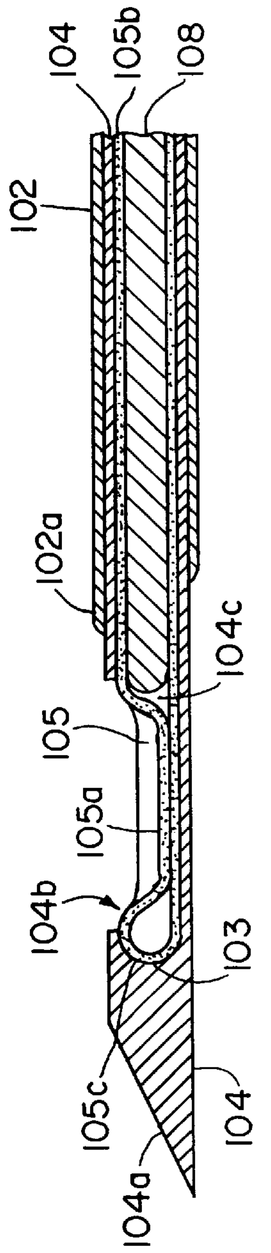
FIG. 3 is a side sectional view of the distal end of the biological agent delivery device with the outer tube 102 retracted to expose the cannula notch 104*b* and the support surface 105*a* of the flexible membrane 105.

Delivery device 100 has a housing 12 with a pair of finger grips 14 extending transverse the longitudinal axis of the housing. A driving member 16 is slideably engaged with a track 20 formed along the longitudinal length of housing 12. The housing 12 has an external cylindrical bore 18 formed therein which extends along the longitudinal axis of the housing 12. A tubular member or cannula 104, having an internal bore 104*c* is mounted within the external cylindrical bore 18 and extends along the longitudinal axis of bore 18. A piston 108 is shown disposed within internal bore 104*c*. Cannula 104 has a solid distal tip 104*a* which is angled for penetration into tissue. A radially lateral opening in the cannula 104 near tip 104*a* forms a cannula notch 104*b* (FIG. 3). An outer tube 102 is secured to housing 12 and is mounted concentrically about cannula 104. Cannula 104 is axially slideable relative to cylindrical bore 18 and outer tube 102 for extending or retracting cannula 104 relative to outer tube 102 in order to enclose or expose cannula notch 104*b*. A flexible membrane 105 having a collapsible support surface 105*a,* a tubular portion 105*b* and a closed distal end 105*c* is positioned coaxially within bore 104*c* of cannula 104. The distal end 105*c* of membrane 105 extends into cannula notch 104*b* and abuts the distal end 103 of cannula notch 104*b*. Flexible membrane 105 extends across the opening of cannula notch 104*b* and prevents bore 104*c* from communicating with regions outside cannula 104 through cannula notch 104*b*. Piston 108 is mounted coaxially within the tubular portion 105*b* of the flexible membrane 105. Piston 108 is axially slideable relative to cannula 104 and tubular portion 105*b* and acts as a displacement member for radially, laterally displacing support surface 105*a*. Since the bore 104*c* within cannula 104 terminates at the distal end 103 of cannula notch 104*b,* piston 108 is restricted from extending past cannula notch 104*b*.

The support surface 105*a* of flexible membrane 105 is located near the distal end 105*c* of the membrane 105 for supporting a quantity of a biological agent 106. The support surface 105*a* is changeable from an undisplaced or collapsed position to a displaced position. When membrane 105 is an undisplaced position, support surface 105*a* is indented downwardly (or inwardly) into flexible membrane 105 to form a pouch with support surface 105*a* contacting the opposite side of the membrane 105. The pouch is typically formed by pushing support surface 105*a* downwardly (inwardly). The support surface 105*a* provides the surfaces of the pouch. Alternatively, the pouch can be preformed into membrane 105 such as by molding. When membrane 105 is in a displaced position, the pouch disappears with the support surface 105*a* being relatively horizontal. Membrane 105 is preferably formed from a flexible polymeric material which can either be stretchable or non-stretchable and can be transparent. Alternatively, membrane 105 can also be formed from other suitable flexible materials such as fabrics. Although tubular portion 105*b* is typically flexible, alternatively, tubular portion 105*b* can be rigid with only the support surface 105*a* being flexible.

The piston 108 and cannula 104 are secured at their respective proximal ends by a piston grip 48, and a cannula grip 50. The proximal end of tubular portion 105*b* of membrane 105 of has a flange 105*d* which secures tubular portion 105*b* to cannula 104 at the proximal end of cannula grip 50. Additionally, if needed, tubular portion 105*b* can be bonded within bore 104*c* with an adhesive. The piston grip 48 and cannula grip 50 are disc-shaped with a diameter which approximates the diameter of the cylindrical bore. The piston grip 48 and the cannula grip 50 are slideably engaged within the housing bore 18. The piston grip 48 and cannula grip 50 have respective channels formed therein through which drive pins 32 and 34 respectively extend for engagement with the proximal ends of the piston 108 and cannula 104 respectively.

Piston drive pin 32 and cannula drive pin 34 both extend through a single elongate slot 128 in housing 12. Housing slot 128 has a notch 128*a* located at its distal end for engaging cannula drive pin 34 when cannula drive pin 34 is in the advanced position. Piston drive pin 32 extends through driving member 16 through a hole 32*a*. Cannula drive pin 34 extends through driving member 16 through an elongate driving member slot 126. Driving member slot 126 has a notch 126*a* located at its distal end for engaging cannula drive pin 34.

The piston 108, cannula 104 and outer tube 102 are preferably formed of rigid sterilizable material such as stainless steel. Other components of the device, including the housing, driving member, piston and cannula grips, etc. are preferably made from low cost plastic material. The use of molded plastic components for the manufacture of the instrument is preferred to lower the cost so that the device can be disposed of after use.

In operation, in order to subcutaneously deliver a quantity of a biological agent 106 to a desired tissue site, the surface 112*a* of tissue 112 is first cut with a scalpel. The tip 104*a* of cannula 104 is then inserted into the incision within tissue 112 while driving member 16 is in a retracted position and the distal end 101 of delivery device 100 is advanced into tissue 112 until reaching a desired location. When driving member 16 is in a retracted position, cannula notch 104*b* is enclosed by outer tube 102 with the tip of piston 108 being at the proximal end of cannula notch 104*b*. Outer tube 102 protects the biological agent 106 and prevents it from spilling out of cannula notch 104*b* prematurely. Alternatively, tip 104*a* of cannula 104 can be inserted into tissue 112 by puncturing the surface 112*a* of tissue 112 with tip 104*a*.

Figure 4:
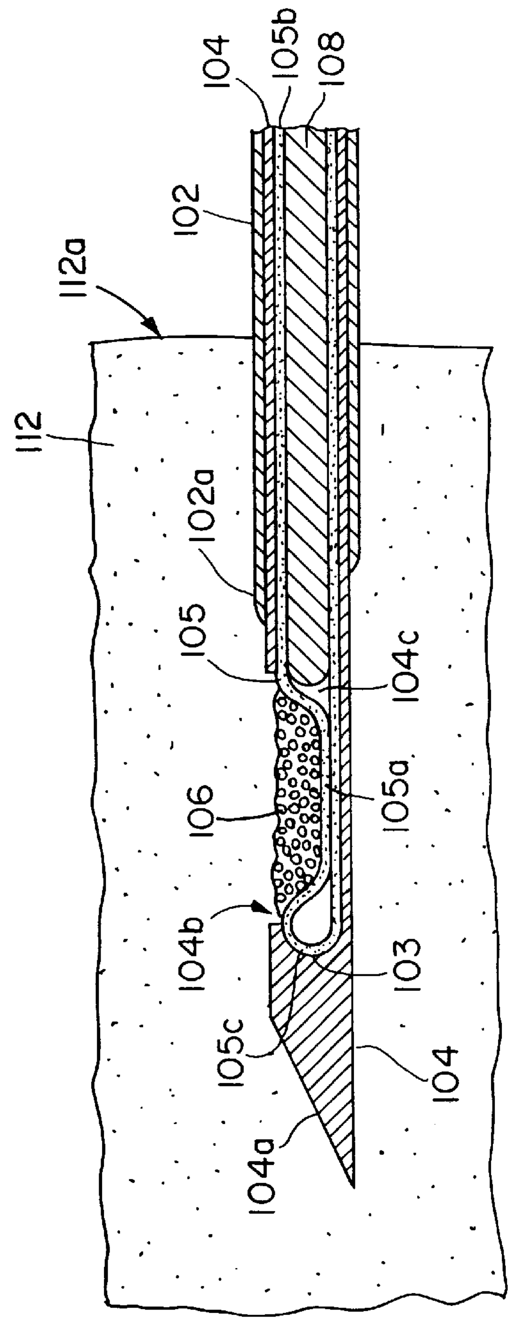
FIGS. 4 and 5 are side sectional views of the distal end of the biological agent delivery device of FIG. 2 depicting the delivery of a quantity of a biological agent to a tissue site.

Driving member 16 is then moved distally along track 20 toward the distal end 101 of delivery device 100. Cannula drive pin 34 is engaged within notch 126*a* of driving member slot 126 and piston drive pin 32 is engaged by hole 32*a*. As the driving member 16 is advanced, cannula 104 is extended from outer tube 102 such that cannula notch 104*b* and the biological agent 106 are exposed beyond the tip 102*a* of outer tube 102 as seen in FIG. 4. At the same time, driving member 16 advances piston 108 by engaging piston drive pin 32 with hole 32*a* such that the cannula 104 and the piston 108 advance together in unison. Cannula 104 is extended until cannula drive pin 34 reaches the distal end of housing slot 128 where cannula drive pin 34 engages housing slot notch 128*a*.

Figure 5:
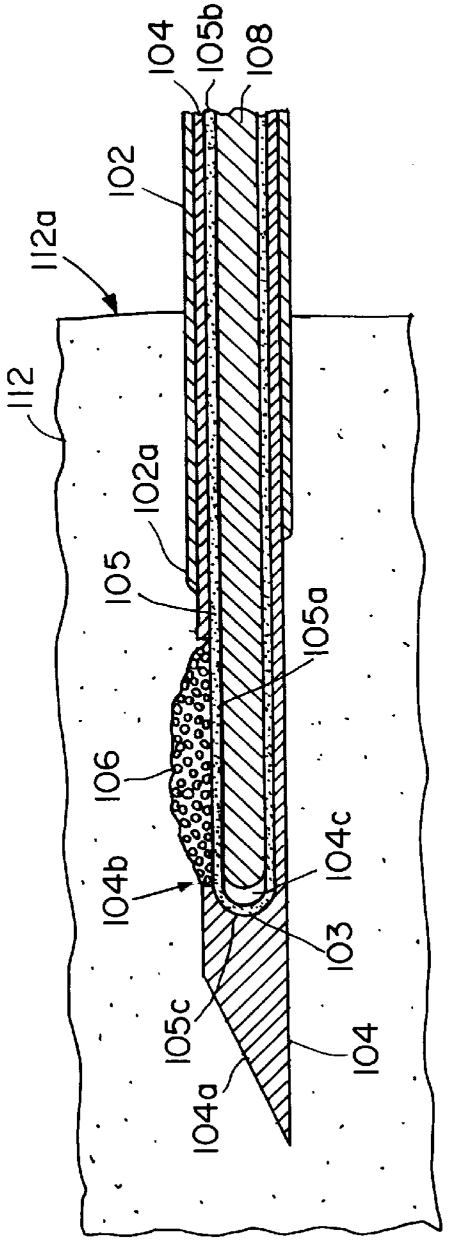

As driving member 16 is further advanced, cannula drive pin 34 disengages from notch 126*a* in driving member slot 126 and piston drive pin 32 is advanced further, thereby advancing piston 108 forward relative to cannula 104. As piston 108 is extended into cannula notch 104*b,* piston 108 laterally displaces the support surface 105*a* of membrane 105 thereby laterally displacing the biological agent 106 from cannula notch 104*b* into the surrounding tissue 112 as seen in FIG. 5. Piston 108 is extended into cannula notch 104*b* until the proximal end of driving member slot 126 reaches cannula drive pin 34, thereby preventing further advancement of driving member 16. Further advancement of piston 108 is also prevented by the distal end 103 of cannula notch 104*b*.

Once the biological agent 106 is deposited into tissue 112, the distal end 101 of delivery device 100 can be removed from tissue 112. To remove distal end 101 from the tissue 112, the cannula 104 and the piston 108 are first retracted relative to outer tube 102 by retracting driving member 16. This leaves behind the biological agent 106 within tissue 112. Distal end 101 of delivery device 100 is then pulled from tissue 112 leaving behind a small puncture wound.

Figure 6:
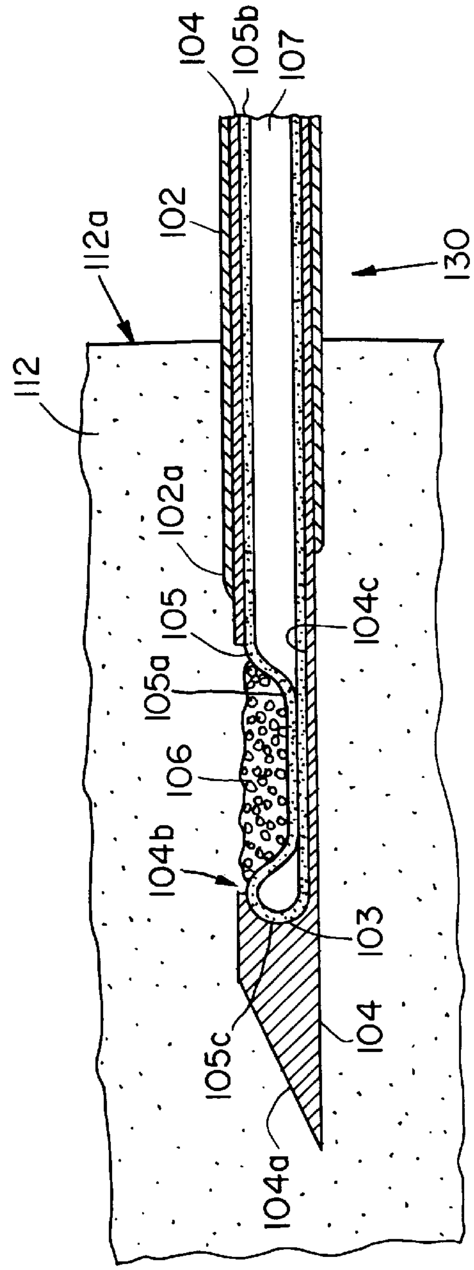
FIGS. 6 and 7 are side sectional views of the distal end of another preferred biological agent delivery device depicting the delivery of a quantity of a biological agent to a tissue site.
Figure 7:
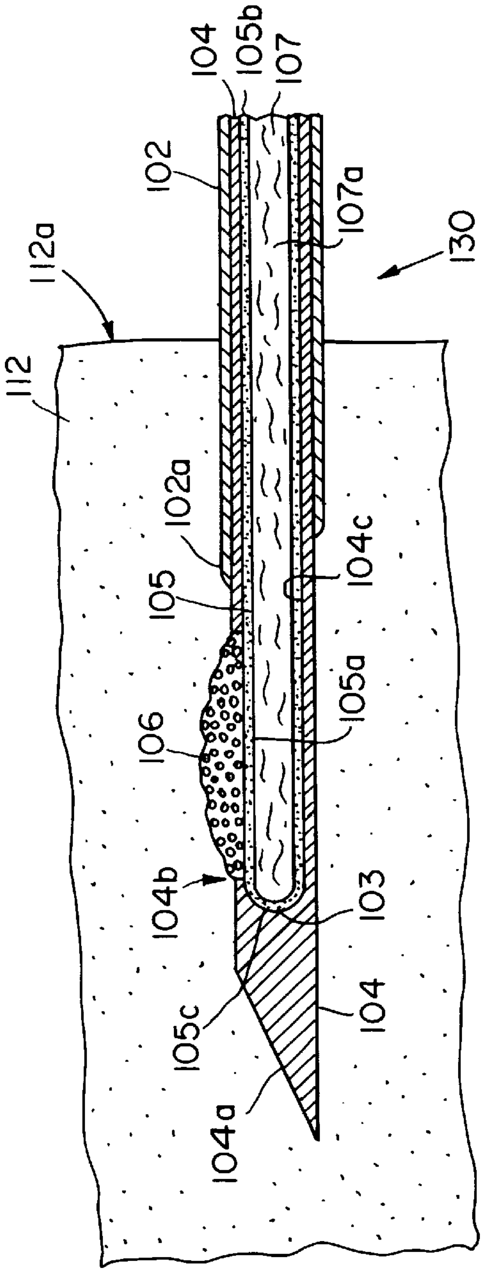

FIGS. 6 and 7 depict the distal end of biological agent delivery device 130 which is another preferred embodiment of the present invention differing from delivery device 100 in that piston 108 and the components associated with advancing and retracting piston 108 are omitted. Instead, in order to deliver a biological agent 106, a fluid 107*a* such as a gas or a liquid is introduced into cavity 107 within membrane 105 to serve as a displacement member in order to laterally displace the support surface 105*a*. If desired, the fluid can outwardly displace support surface 105*a* past the outer surface of cannula 104 thereby forming an outward bulge in membrane 105. The fluid is preferably air if a gas is employed or saline solution if a liquid is employed and is preferably introduced into cavity 107 by a piston/plunger type mechanism or a closed loop pump mechanism within or attached to delivery device 130. Such a mechanism can be a syringe-type device or a calibrated ampoule-type device. Alternatively, the fluid can be introduced from a reservoir by a pump or from a pressurized tank and can be any other suitable gas or liquid.

Figure 8:
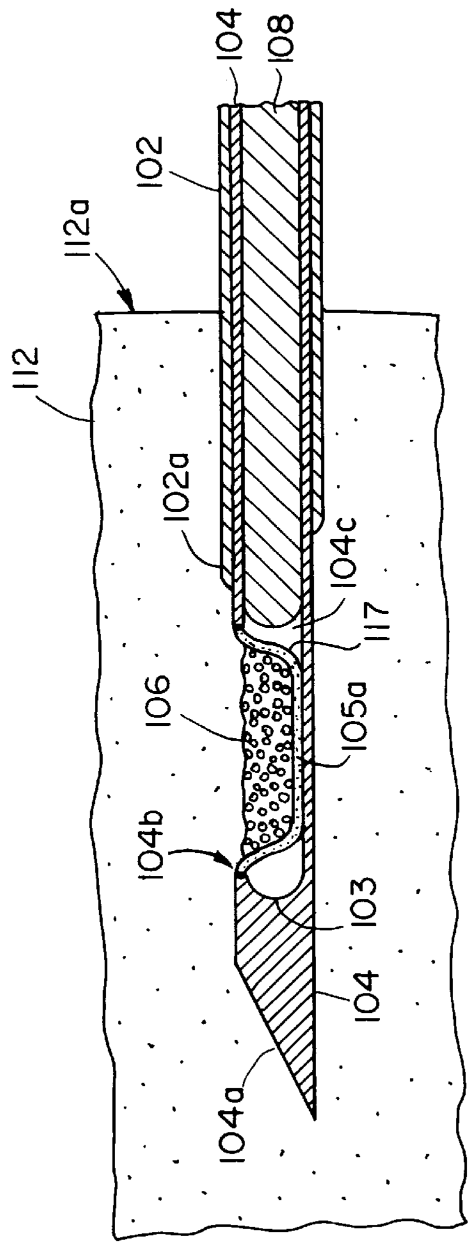
FIG. 8 is a side sectional view of the distal end of yet another preferred biological agent delivery device.
Figure 9:
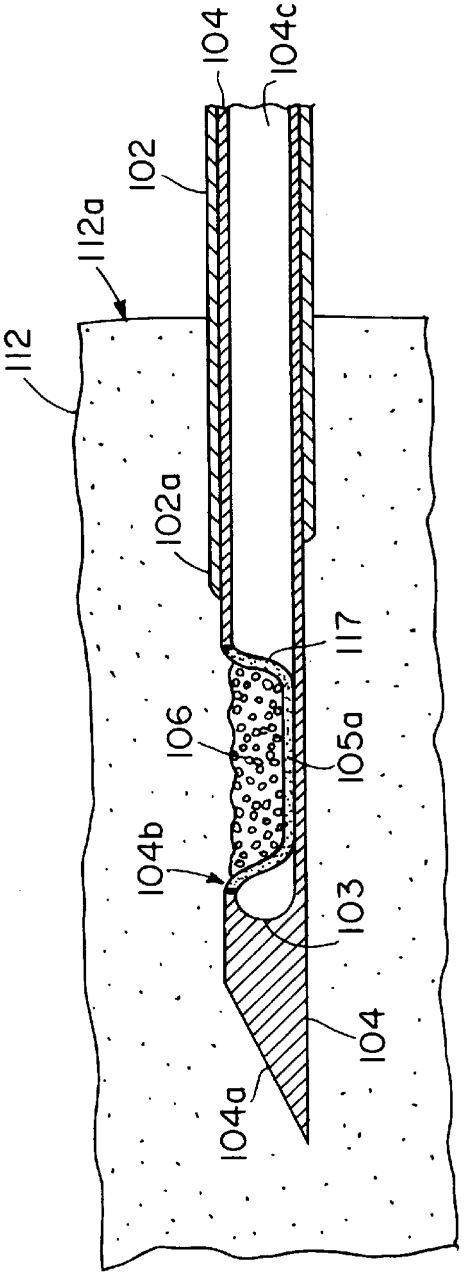
FIG. 9 is a side sectional view of the distal end of still another preferred biological agent delivery device.

Referring to FIGS. 8 and 9, flexible membrane 117 differs from flexible membrane 105 in that it does not include a tubular portion 105*b* but consists of a flexible membrane extending across and sealed over the lateral opening of cannula notch 104*b*. As a result, in the embodiment shown in FIG. 8, the piston 108 contacts and slides within bore 104*c* of cannula 104. In the embodiment depicted in FIG. 9, the support surface 105*a* of membrane 117 is laterally displaced by a fluid such as gas or liquid introduced into bore 104*c* of cannula 104.

Figure 10:
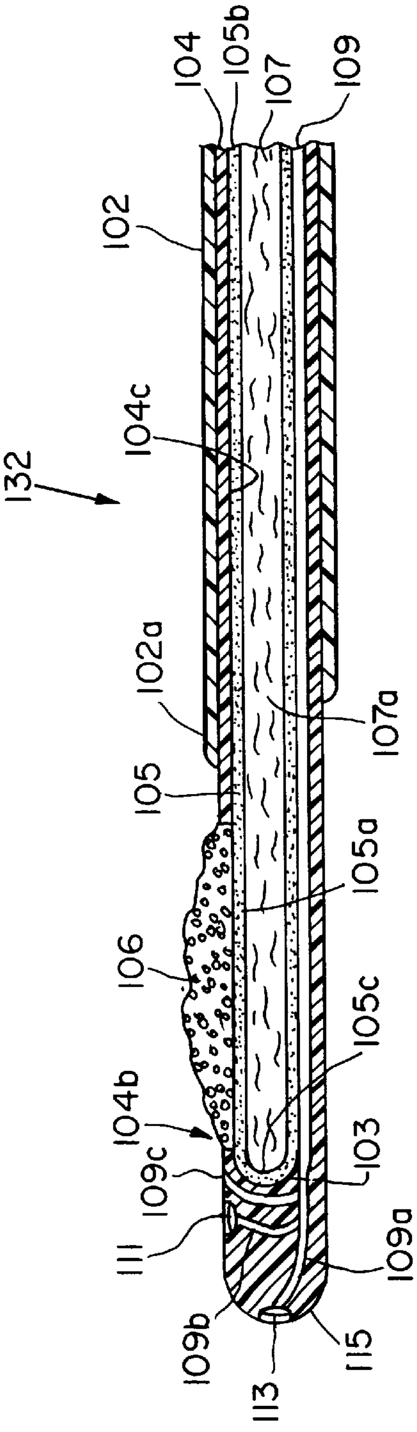
FIG. 10 is a side sectional view of the distal end of still another preferred biological agent delivery device.

Referring to FIG. 10, biological agent delivery device 132 is a flexible catheter for insertion into body cavities of a patient. In order to provide flexibility of the catheter, the cannula 104 and outer tube 102 are made of flexible material. As in delivery device 130, the support surface 105*a* of flexible membrane 105 is displaced by fluid introduced into cavity 107. Cannula 104 has a blunt tip 115 to facilitate the passage of delivery device 132 through body cavities. Although delivery device 132 is shown to include flexible membrane 105, alternatively, flexible membrane 117 may be employed instead.

An optional fiber optic bundle 109 including optical fibers 109*a*, 109*b* and 109*c* is positioned within bore 104*c* of cannula 104 alongside tubular portion 105*b* of membrane 105. Optical fiber 109*c* is directed laterally with respect to cannula 104 to provide light to a desired drug delivery site for optimized drug absorption. Illumination is also useful when delivering cells, subcellular extracts, plasmids or gene products for genetic therapy because it facilitates gene transfer. In addition, other forms of electromagnetic radiation can be delivered by optical fiber 109*c*, for example, ultra-violet light for altering cell membranes or for sterilization, or to increase cell membrane permeability with blue light. Furthermore, optics for viewing the delivery site are provided by laterally positioning optical fiber 109*b* and lens 111. Finally, optics for forward viewing are provided by optical fiber 109*a* and lens 113.

Although the present invention biological agent delivery device has been described for primarily delivering particulate or liquid biological agents, biological agents in pellet form can also be delivered. The term “biological agent” is meant to encompass any substance that can be introduced into tissue or a body cavity for treating a patient such as drugs, microspheres, cells, cell clusters, cells transfected with foreign DNA, cellular components, cellular extracts or gene products. The term “drug” as used herein is intended to have a broad construction so as to include any type of medication capable of being administered in the manner described herein. When biological agents in a liquid form are delivered, a sealing arrangement can be provided around cannula notch 104*b* to reduce the possibility that liquid will not leak prematurely from cannula notch 104*b* when outer tube 102 encloses cannula notch 104*b*.

Equivalents

While this invention has been particularly shown and described with references to preferred embodiments thereof, it will be understood by those skilled in the art that various changes in form and details may be made therein without departing from the spirit and scope of the invention as defined by the appended claims. For example, other mechanisms can be employed for advancing and retracting cannula 104 and piston 108. Such mechanisms can include motor or hand-operated gears and power screws, or fluid operated cylinders. In addition, the present invention delivery device can be employed for implanting non-therapeutic, solid or rigid objects into tissue or body cavities such as tracking devices, radio transmitters or pumps.

What is claimed is:

1. A biological agent delivery device comprising:

a cannula having a longitudinally extending wall and a rigid closed pointed tip at a distal end with a notch in said wall near the distal end forming a lateral opening in the cannula wall;

a flexible membrane having a lateral support surface for supporting a biological agent, the membrane being disposed within the cannula notch, the support surface forming a laterally facing pouch capable of being displaced laterally inwardly and outwardly within the cannula notch for containing and laterally displacing the biological agent; and a displacement member disposed within the wall of the cannula for displacing the support surface of the membrane laterally with respect to the cannula to deliver the biological agent.

2. The delivery device of claim 1 further comprising an outer tube mounted concentric with the cannula for relative movement with respect to the cannula or enclosing or exposing the cannula notch.

3. The delivery device of claim 1 in which the displacement member comprises a piston.

4. The delivery device of claim 1 in which the displacement member comprises a volume of fluid.

5. The delivery device of claim 4 in which the fluid is a liquid.

6. The delivery device of claim 4 in which the fluid is a gas.

7. The delivery device of claim 1 in which the support surface forms a pouch when the flexible membrane is in a non-displaced state.

8. The delivery device of claim 7 in which the pouch is preformed.

9. The delivery device of claim 1 in which the flexible membrane extends within the cannula and comprises a tubular member having a closed distal end, the support surface of the membrane being located near said closed distal end and positioned within the cannula notch.

10. The delivery device of claim 1 further comprising fiber optics within the cannula for delivering radiation to a desired tissue site.

11. The delivery device of claim 10 further comprising a lens associated with the fiber optics for enabling viewing of regions external to the cannula.

12. A biological agent delivery device comprising:

a cannula having a longitudinally extending wall and a rigid closed pointed tip at a distal end with a notch in said wall near the distal end forming a lateral opening in the cannula wall;

a flexible membrane having a lateral support surface for supporting a biological agent, the membrane being disposed within the cannula notch, the support surface forming a laterally facing pouch capable of being displaced laterally inwardly and outwardly within the cannula notch for containing and laterally displacing the biological agent; and a displacement member disposed within the wall of the cannula for displacing the support surface of the membrane laterally with respect to the cannula to displace the biological agent; and an outer tube mounted concentric with the cannula for relative movement with respect to the cannula for enclosing or exposing the cannula notch.

13. The delivery device of claim 12 in which the displacement member comprises a piston.

14. The delivery device of claim 12 in which the displacement member comprises a volume of fluid.

15. The delivery device of claim 14 in which the fluid is a liquid.

16. The delivery device of claim 14 in which the fluid is a gas.

17. The delivery device of claim 12 in which the support surface forms a pouch when the flexible membrane is in a non-displaced state.

18. The delivery device of claim 17 in which the pouch is preformed.

19. The delivery device of claim 12 in which the flexible membrane extends within the cannula and comprises a tubular member having a closed distal end, the support surface of the membrane being located near said closed distal end and positioned within the cannula notch.

20. The delivery device of claim 12 further comprising fiber optics within the cannula for delivering radiation to a desired tissue site.

21. The delivery device of claim 20 further comprising a lens associated with the fiber optics for enabling viewing of regions external to the cannula.

22. A method of delivering a biological agent to a tissue site comprising the steps of:

providing a cannula having a longitudinally extending wall and a rigid closed pointed tip at a distal end with a notch in said wall near the distal end forming a lateral opening in the cannula wall;

supporting a biological agent on a lateral support surface of a flexible membrane, the membrane being disposed within the cannula notch, the support surface forming a laterally facing pouch capable of being displaced laterally inwardly and outwardly within the cannula notch for containing and laterally displacing the biological agent;

inserting the distal end of the cannula into the tissue site; and laterally displacing the support surface of the membrane with respect to the cannula with a displacement member disposed within the wall of the cannula to deliver the biological agent to the tissue site.

23. The method of claim 22 further comprising the step of enclosing the cannula notch with an outer tube mounted concentric with the cannula before insertion of the distal end of the cannula into the tissue site.

24. The method of claim 23 further comprising the step of extending the cannula to expose the cannula notch beyond the outer tube after insertion of the distal end of the cannula into the tissue site.

25. The method of claim 22 further comprising the step of extending the flexible membrane within the cannula, the membrane comprising a tubular member having a closed distal end, the support surface of the membrane being located near said closed distal end and positioned within the cannula notch.

26. The method of claim 22 further comprising the step of delivering radiation to a desired tissue site with fiber optics.

27. The method of claim 22 further comprising the step of viewing regions external to the cannula with fiber optics.

28. The method of claim 22 further comprising the step of forming the support surface of the flexible membrane into a pouch.

29. A subcutaneous delivery device comprising:

a cannula having a longitudinally extending wall and a rigid closed pointed tip at a distal end with a notch in said wall near the distal end forming a lateral opening in the cannula wall;

a flexible membrane having a lateral support surface supporting a product to be delivered, the membrane being disposed within the cannula notch, the support surface forming a laterally facing pouch capable of being displaced laterally inwardly and outwardly within the cannula notch for containing and laterally displacing the biological agent; and a displacement member disposed within the wall of the cannula for displacing the support surface of the membrane laterally with respect to the cannula to deliver the product.

* * * * *